United States Patent [19]

Kharasch et al.

[11] 3,976,678
[45] Aug. 24, 1976

[54] 2,3-DISUBSTITUTED LEVULINALDEHYDES

[75] Inventors: Norman Kharasch, Los Angeles, Calif.; Ahmed I. Khodair, Cairo, Egypt

[73] Assignee: Intra-Science Research Foundation, Los Angeles, Calif.

[22] Filed: June 19, 1975

[21] Appl. No.: 588,187

[52] U.S. Cl.............................. 260/465.6; 260/404; 260/465.4; 204/158 HA
[51] Int. Cl.²...................................... C07C 121/34
[58] Field of Search................... 260/465.6

[56] References Cited
UNITED STATES PATENTS

| | | | |
|---|---|---|---|
| 3,832,380 | 8/1974 | Matsui et al. | 260/464 X |
| 3,835,179 | 9/1974 | Schaub et al. | 260/464 X |
| 3,845,042 | 10/1974 | Strike et al. | 260/464 X |
| 3,853,854 | 12/1974 | Weinshenker et al. | 260/464 X |
| 3,870,747 | 3/1975 | Wendler et al. | 260/464 X |
| 3,872,107 | 3/1975 | Crabbe | 260/464 X |

*Primary Examiner*—Joseph Paul Brust
*Attorney, Agent, or Firm*—Martin A. Voet

[57] ABSTRACT

Novel 2,3-disubstituted levulinaldehydes I are prepared in seven steps from readily available acrylates and acetoacetic esters.

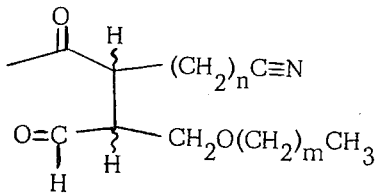

They are useful intermediates in the preparation of prostaglandins.

2 Claims, No Drawings

2,3-DISUBSTITUTED LEVULINALDEHYDES

This invention relates to new 2,3-disubstituted levulinaldehydes useful as intermediates for the synthesis of cyclopentane derivatives, and to a process for their preparation from known starting materials. More particularly, it is concerned with the preparation of compounds which can be eventually converted to the class of compounds known to those skilled in the art as "prostaglandins". Prostaglandins and their analogues have been shown to have valuable therapeutic pharmacological properties.

BACKGROUND OF THE INVENTION

The compounds contemplated to be provided by the instant invention are 2,3-disubstituted levulinaldehydes of the general formula:

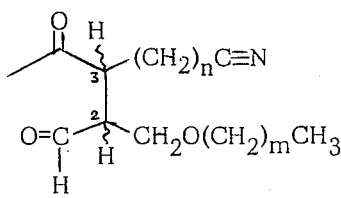

I wherein $n$ represents an integer from 5 to 8 inclusive and $m$ represents zero or an integer from 1 to 5 inclusive.

As will be apparent to those skilled in the art, the structure shown in formula I has two centres of chirality, these two centres of chirality being at the carbon atoms in positions 2 and 3 respectively. Accordingly, all isomers of formula I, and mixtures thereof, are within the scope of the present invention.

Compounds of formula I are intermediates in the synthesis of highly biologically active cyclopentane derivatives known to those skilled in the art as "prostaglandins". Prostaglandins possess potent activities in the inhibition of gastric acid secretion, the production of hypotension, bronchodilation, the stimulation of uterine contraction, the production of hypocholesteraemia and hypolipidaemia and the stimulation of luteolysis.

The present invention seeks to provide intermediates useful in the preparation of prostaglandins of the $PG_1$ series, that is prostaglandins containing a double bond in the 13, 14 position of prostanoic acid, for example, $PGE_1$, $PGA_1$, $PGB_1$, $PGF_{1\alpha}$, or $PGF_{1\beta}$.

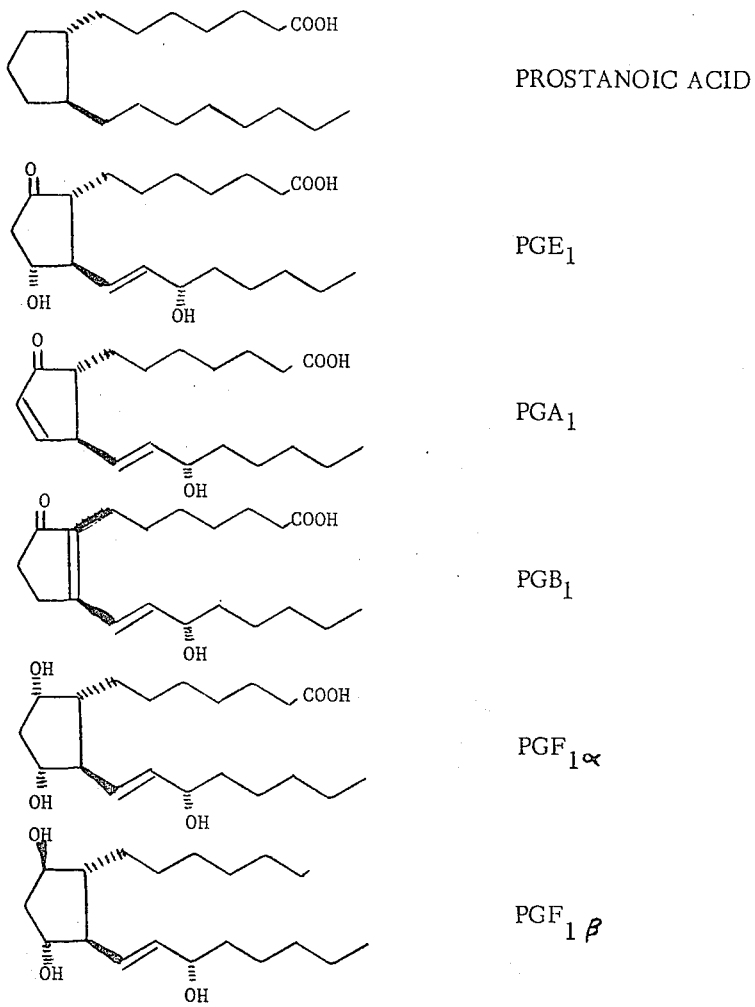

2,3-Disubstituted levulinaldehydes (D. P. Strike & H. Smith, U.S. Pat. No. 3,718,667) have previously been used in the synthesis of prostaglandins, but these compounds, because of their method of preparation, were restricted to the basic prostanoic acid structure, that is containing no 13,14-carbon-carbon double bond.

Although a number of methods are now available to the hereinbefore mentioned prostaglandins, (for example Merck & Co. Inc., U.S. Patent Application Ser. No. 201,979 of Nov. 24, 1971) a clear need exists for improved means, by fewer reaction steps and more readily accessible starting materials, to provide these therapeutically active compounds. The present invention provides such a means, requiring a smaller number of reaction steps, using inexpensive commercially available materials, to make 2,3-disubstituted levulinaldehydes, precursors for the hereinbefore mentioned prostaglandins.

It is the primary object of this invention, therefore, to provide 2,3-disubstituted levulinaldehydes by total synthesis from readily accessible starting materials, for use as intermediates in the synthesis of prostaglandins.

DESCRIPTION OF THE INVENTION AND PREFERRED EMBODIMENT

The process of the invention for the preparation of 2,3-disubstituted levulinaldehydes of formula I is illustrated schematically as follows:

wherein $m$ and $n$ are as hereinbefore defined, $R^1$ represents a methyl or ethyl group, $R^2$ represents a methyl or ethyl group, $R^3$ represents a methyl or ethyl group and X is chlorine, bromine or iodine.

The reaction of an acrylate of formula II with an alcohol of formula III is carried out in the presence of mercuric acetate to yield an intermediate mercuriacetate of formula VIa. This intermediate of formula VIa is then reacted with bromine, preferably in the presence of inert organic solvent, for example chloroform, preferably in the presence of light, for example light from a photoflood lamp, and preferably at an elevated temperature, for example at 50° to 57°C, to yield α-bromo-β-alkoxypropionates of formula VIb.

The substituted acetoacetic esters of formula VII are prepared by reacting the acetoacetate of formula IV with a base strong enough to remove a proton from the acetoacetate, for example and preferably potassium tert. butoxide, preferably in the presence of inert organic solvent, for example tert. butanol, and preferably at a temperature between 0° and 50°C, advantageously at room temperature, followed by addition of a ω-halonitrile of formula V, preferably a ω-bromo- or ω-iodonitrile, preferably in an inert organic solvent, for example tert. butanol, preferably at a temperature between 0° and 50°C, advantageously at room temperature, preferably followed by heating, for example the reflux temperature of the solvent, to the intermediately formed salt of the acetoacetate IV.

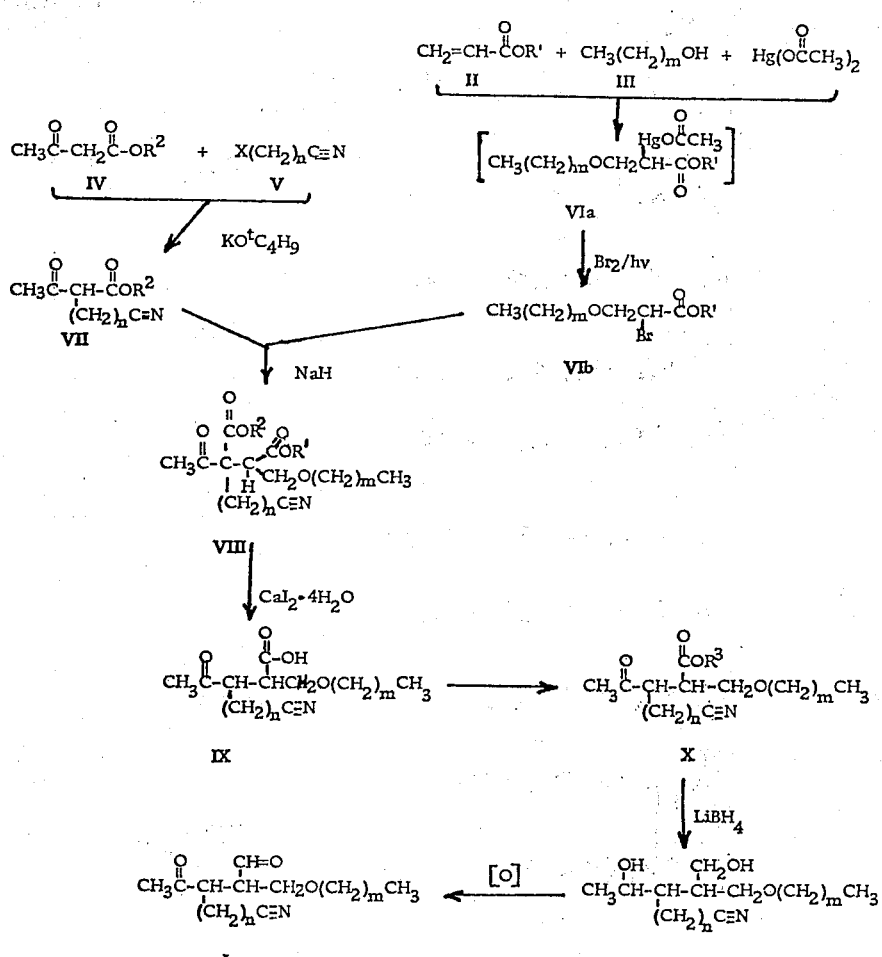

The substituted acetoacetates of formula VII are reacted with a base strong enough to remove a proton from the acetoacetate, without affecting the other functional groups present, preferably sodium hydride, preferably in the presence of an inert organic solvent, for example a mixture of tetrahydrofuran and hexamethylphosphoramide, preferably in an inert atmosphere, for example under nitrogen or argon, and preferably at a lower temperature, for example at 0°C. The intermediately formed salt of the substituted acetoacetate is reacted with an α-bromo-β-alkoxy propionate of formula VIb, preferably at a temperature between 0° and 50°C, advantageously at room temperature, to yield disubstituted acetoacetates of formula VIII.

The disubstituted acetoacetates of formula VIII are decarboxylated to 2,3-disubstituted levulinic acids of formula IX by means of reagents capable of removing the $COOR^2$ group and dealkylating the $COOK^1$ group of compounds of formula VII, preferably calcium iodide tetrahydrate, optionally in the presence of a high boiling inert organic solvent, for example diglyme, preferably at an elevated temperature, for example 150°C and preferably in an inert atmosphere, for example under nitrogen or argon.

The 2,3-disubstituted levulinic acids of formula IX are esterified to the corresponding esters of formula X by known methods for the conversion of the carboxy group to the carboxyalkyl group, for example and advantageously with a diazoalkane $R^3 = N_2$ ($R^3$ being as hereinbefore defined) in an inert organic solvent, preferably an ether, for example diethyl ether, preferably at ambient temperature.

The 2,3-disubstituted levulinates of formula X are reduced to 2,3-disubstituted-1,4-pentanediols of formula XI by using means and conditions capable of simultaneously reducing carbonyl to hydroxymethylene and carboxylic esters to hydroxymethyl groups without affecting carbon-nitrogen triple bonds. The reduction is preferably effected by lithium borohydride, preferably in the presence of inert organic solvent, for example an ether, for example tetrahydrofuran, at an elevated temperature, advantageously at the reflux temperature of the reaction mixture.

The 2,3-disubstituted-1,4-pentanediols of formula XI are oxidized using agents known to convert hydroxy groups to carbonyl groups without affecting carbon-nitrogen triple bonds, for example chromium trioxide in dichloromethane and pyridine (known to those skilled in the art as "Collins' reagent") to yield 2,3-disubstituted levulinaldehydes of formula I.

The acrylates of formula II, the acetoacetates of formula IV, the alcohols of formula III and the ω-halonitriles of formula V are readily available commercially or easily accessible by known methods. By the term "known methods" as used in this specification is meant methods heretofore used or described in the literature.

As will be readily appreciated by those skilled in the art, the isomeric forms of the compounds of the invention arising from the aforementioned centres of chirality may be separated by the application or adaptation of known methods, for example diastereoisomers may be separated by chromatography using selective adsorption from solution or from the vapour phase onto suitable absorbents.

The preferred compound of the present invention is the compound within formula I as hereinbefore defined wherein $n$ is 6 and $m$ is zero.

The following Example illustrates the compounds of the present invention and their preparation.

EXAMPLE I 3-(6-cyanohexyl)-2-methoxymethyl-levulinaldehyde i. Preparation of Methyl α-bromo-β-methoxypropionate To a solution of 45 g. of methanol (dried over magnesium) and 33.7 g. of methylacrylate was added 120 g. of mercuric acetate. The mixture was allowed to stand at room temperature for three days with occasional shaking (after this period a small amount of unreacted mercuric acetate remained). The reaction mixture was cooled in an ice-bath and a solution of 45 g. of potassium bromide in 150 ml. of water was added, dropwise with stirring, during 25 mins. The heavy white oil which separated was extracted with 20 ml. of chloroform and the aqueous layer extracted with two further 50 ml. portions of chloroform. The combined chloroform extracts were washed with four 60 ml. portions of distilled water, dried and filtered. The filtrate in a 600 ml. beaker was exposed to two No. 2 photoflood lamps which were mounted in suitable reflectors as near the surface of the solution as possible and maintained at 50° to 57°C whilst 56.3 g. of bromine was added, with stirring, at such a rate as to keep up with its consumption. When all the bromine had been consumed, the reaction mixture as cooled for 15 mins. in an ice-bath and the precipitated mercuric bromide was removed by filtration and washed carefully with chloroform. The filtrate was concentrated under reduced pressure to yield an oil. Infra-red and proton NMR spectroscopy confirmed the desired product was obtained. The product, Methyl α-bromo-β-methoxy propionate (68.9 g., 100% yield based on bromine) showed a single peak by gas-liquid chromatography. It was desirable to freshly distil the product before use in the next reaction.

ii. Preparation of Methyl 2-acetyl-8-cyano-octanoate

To 50 ml. of tert-butanol (dried by refluxing over sodium) was added 2.032 g. of small pieces of freshly cut potassium and the mixture heated with stirring until all the potassium had dissolved. The solution was cooled to room temperature and 11.6 g. of freshly distilled methyl acetoacetate in 5 ml. of dry tert.-butanol was added in one portion. Then 9.5 g. of 7-bromoheptanonitrile (freshly distilled) in 10 ml. of dry tert.-butanol as added dropwise over 0.5 hr. After the addition, the reaction mixture was stirred at room temperature for 1 hr. then refluxed for an additional 5 hrs. Most of the solvent was removed in vacuo and the residue taken up in 50 ml. of benzene, then poured over water. The organic layer was separated and the aqueous layer was extracted four times with 50 ml. portions of benzene. The combined organic extracts were washed with water, then brine, and dried over anhydrous magnesium sulphate. Evaporation of the solvent in vacuo gave an oil which on distillation gave a product b.p. 180°–184°C/4 mm. of mercury. Infra-red and proton NMR spectroscopy were consistent with the desired product. The product, Methyl 2-acetyl-8-cyano-octanoate (10.3 g., 91.5% yield) exhibited a single peak by gas-liquid chromatography.

iii. Preparation of Dimethyl 2-acetyl-2-(6-cyanohexyl)-3-methoxymethyl succinate To a stirred solution of 23.23 g. of methyl 2-acetyl-8-cyano-octanoate in 80 ml. of a mixture of 80 : 20 dry tetrahydrofuran and dry hexamethylphosphoramide under nitrogen was added portionwise a suspension of 5.445 g. of sodium hydride in a small amount of the above tetrahydrofuran/hexamethylphosphoramide mixture, while cooling in an ice-bath. When the evolution of gas had ceased, 40.766 g. of freshly distilled methyl α-bromo-β-methoxy propionate was added in one portion and the reaction mixture stirred at room temperature for 22 hrs. After this period, 50 ml. of a 50 : 50 mixture of diethyl ether/dichloromethane was added and the contents poured onto water. The organic layer was separated and the aqueous layer was extracted 4 times with 50 ml. portions of the 50 : 50 mixture of diethyl ether/dichloromethane. The combined organic extracts were washed 3 times with 40 ml. portions of water, once with brine and dried over anhydrous magnesium sulphate. Removal of the solvent by means of a rotary evaporator followed by distillation of the excess bromo ester gave crude product (29.6 g.). This was purified by chromatography on silica gel as detailed below.

A sample of 28 g. of the above crude product was placed on a column of 150 g. of silica gel and eluted with a mixture of 60 : 40 diethyl ether/hexane. The first 1250 ml. of eluate contained low boiling material and unreacted starting material and was discarded. The following 1000 ml. of eluate on evaporation in vacuo gave the desired product, Dimethyl 2-acetyl-2-(6-cyanohexyl)-3-methoxymethyl succinate (11.06 g., 33% yield).

Alternatively, the separation was accomplished more efficiently and cleanly by adopting the following procedure.

A sample of 3.42 g. of the crude product obtained in another run was placed on a column containing 50 g. of silica gel and eluted as follows:

| Fraction | Solvent | Volume of eluate collected (mls.) | Weight of isolated material (g.) |
|---|---|---|---|
| 1 | 80:20 hexane/diethyl ether | 200 | — |
| 2 | 70:30 hexane/diethyl ether | 300 | 0.013 |
| 3 | 70:30 hexane/diethyl ether | 450 | 0.18 |
| 4 | 70:30 hexane/diethyl ether | 200 | 0.209 |
| 5 | 60:40 hexane/diethyl ether | 100 | 0.250 |
| 6 | 60:40 hexane/diethyl ether | 200 | 0.574 |
| 7 | 60:40 hexane/diethyl ether | 100 | 0.375 |
| 8 | 54:36:10 hexane/diethyl ether/ethyl acetate | 500 | 1.131 |

Fractions 7 and 8 contained the desired product, Dimethyl 2-acetyl-2-(6-cyanohexyl)-3-methoxymethyl succinate (1.506 g., 37% yield).

The proposed structure for the product was confirmed by proton NMR, Infra-red and mass spectral data.

iv. Preparation of 3-acetyl-9-cyano-2-methoxymethyl nonanoic acid a. 11.06 g. of dimethyl 2-acetyl-2-(6-cyanohexyl)-3-methoxymethyl succinate was heated with 11.2 g. of calcium iodide tetrahydrate at 150°C for 4 hrs. under a nitrogen atmosphere. At the end of the heating period the flask was cooled to room temperature and 30% sulphuric acid was added. The mixture was shaken vigorously and the supernatant decanted into a separatory funnel. This procedure was repeated until all the gummy residue had decomposed. The product was isolated by extraction five times with a 50 : 50 mixture of diethyl ether/dichloromethane. The combined organic extracts were extracted four times with 6% aqueous potassium hydroxide solution and once with water. The combined aqueous extracts were acidified with 30% sulphuric acid and the liberated organic acid was extracted with 4 times 50 ml. portions of 50 : 50 diethyl ether/dichloromethane mixture. The combined organic extracts were washed with water until acid free, then with saturated brine and dried over anhydrous magnesium sulphate. Removal of the solvent in vacuo gave crude product (5.3 g.) as an oil. The crude acid was then purified by chromatography on silica gel or esterified with diazomethane and then purified by chromatography.

b. A 2.3 g. sample of the crude acid obtained above was placed on a column containing 50 g. of silica gel and eluted as follows:

| Fraction | Solvent | Volume of eluate collected (mls.) | Weight of isolated material (g.) |
|---|---|---|---|
| 1 | 60:40 hexanes/diethyl ether | 160 | 0.016 |
| 2 | 60:40 hexanes/diethyl ether | 160 | — |
| 3 | 60:40 hexanes/diethyl ether | 160 | — |
| 4 | 30:70 hexanes/diethyl ether | 200 | 0.050 |
| 5 | 30:70 hexanes/diethyl ether | 200 | 0.407 |
| 6 | diethyl ether | 200 | 0.865 |
| 7 | diethyl ether | 200 | 0.256 |
| 8 | 90:10 diethyl ether/ethyl acetate | 350 | 0.131 |

Fractions 5 to 8 inclusive contained the desired product, 3-Acetyl-9-cyano-2-methoxymethyl nonanoic acid (1.725 g., 45.5% yield). Infra-red and proton NMR spectroscopy were in agreement with the proposed structure.

v. Preparation of Methyl 3-acetyl-9-cyano-2-methoxymethyl nonanoate a. To a solution of 0.5 g. of excess diazomethane in 50 ml. of dry diethyl ether was added a solution of 1.7 g. of pure 3-acetyl-9-cyano-2-methoxymethyl nonanoic acid [prepared as described in Example I(iv) (b)] in 25 ml. of dry diethyl ether. The resulting solution was allowed to stand at ambient temperature for 18 hrs., during which time a small amount of solid precipitated. The solid was removed by filtration and the filtrate evaporated in vacuo to give an oil. Infra-red and proton NMR spectroscopy and are in agreement with the proposed structure. No molecular ion was observed in the mass spectrum, but $M^+-31$ and $M^+-32$ were observed and the fragmentation pattern is in agreement with the proposed structure. The product, Methyl 3-acetyl-9-cyano-2-methoxymethyl nonanoate (1.75 g., 98% yield) exhibited two partially separable peaks at retention times 5.3 and 5.6 min. (5′ × ⅛″, 3% OV-17, 205°C and nitrogen flow 30 ml./min.).

b. Alternatively, the crude acid obtained in Example I (iv) (a) was converted to its methyl ester and this was purified by chromatography. In this way, a solution of 0.25 g. of excess diazomethane in 25 ml. of dry diethyl ether was added to a solution of 0.8 g. of crude 3-acetyl-9-cyano-2-methoxymethyl nonanoic acid [prepared as described in Example I (iv) (a)] in 15 ml. of dry diethyl ether. The resulting solution was allowed to stand at ambient temperature for 18 hrs., during which time a small amount of solid precipitated. The solid was removed by filtration and the filtrate evaporated in vacuo to give an oil (0.82 g.).

A sample of 0.4 g. of the crude ester obtained above was placed on a column containing 10 g. of silica gel and eluted as follows:

| Fraction | Solvent | Volume of eluate collected (mls.) | Weight of isolated material (g.) |
| --- | --- | --- | --- |
| 1 | 80:20 hexanes/ether | 200 | — |
| 2 | 70:30 hexanes/ether | 200 | — |
| 3 | 70:30 hexanes/ether | 200 | 0.076 |
| 4 | 70:30 hexanes/ether | 200 | 0.066 |
| 5 | 70:30 hexanes/ether | 200 | 0.023 |
| 6 | 70:30 hexanes/ether | 200 | — |
| 7 | ether | 200 | 0.103 |

Fractions 3 to 5 inclusive contained the desired product, Methyl 3-acetyl-9-cyano-2-methoxymethyl nonanoate (0.165 g., 24% overall yield from Dimethyl 2-acetyl-2-(6-cyanohexyl)-3-methoxymethyl succinate) identical in all respects to that obtained by the alternative method (a).

vi. Preparation of 3-(6-cyanohexyl-2-methoxymethyl-1,4-pentanediol

To a mixture of 0.41 g. of lithium borohydride in 40 ml. of dry tetrahydrofuran was added, with stirring at room temperature, a solution of 0.845 g. of methyl 3-acetyl-9-cyano-2-methoxymethyl nonanoate [prepared as in Example I (v) (a) or Example I (v) (b)] in 5 ml. of dry tetrahydrofuran. The reaction mixture was heated under reflux for 5 hrs. The reaction mixture was then cooled to room temperature and poured slowly and carefully into a mixture of 100 g. of ice and 15 ml. of concentrated hydrochloric acid. The organic material was separated by extraction with 6 30 ml. portions of a mixture of 50 : 50 diethyl ether/dichloromethane. The combined organic extracts were carefully washed with water until free of acid, then with brine and dried over anhydrous sodium sulphate. Removal of the solvents in vacuo at room temperature gave an oil, 3-(6-cyanohexyl)-2-methoxymethyl-1,4-pentanediol (0.737 g., 96% yield). Infra-red and proton NMR spectroscopy was in agreement with the proposed structure.

vii. Preparation of 3-(6-cyanohexyl)-2-methoxymethyl levulinaldehyde

To a mixture of 1.874 g. of pyridine (dried over barium oxide) and 60 ml. of dichloromethane (dried over calcium chloride) was added in one portion 1.237 g. of chromium trioxide (dried over phosphorus pentoxide). The mixture was stirred at room temperature for 15 mins. then 0.255 g. of 3-(6-cyanohexyl)-2-methoxymethyl-1,4-pentanediol in 5 ml. of dry dichloromethane was added in one portion. The reaction mixture was stirred at room temperature for 0.5 hr., at the end of which the supernatant was decanted into a separatory funnel. The residue was washed several times with diethyl ether (total 150 ml.). The combined organic solutions were washed three times with 20 ml. portions of 5% aqueous potassium hydroxide solution, twice with 20 ml. portions of 5% hydrochloric acid, once with 20 ml. of sodium bicarbonate and finally with 15 ml. of brine. Drying over anhydrous magnesium sulphate and removal of the solvent in vacuo gave the desired 3-(6-cyanohexyl)-2-methoxymethyl levulinaldehyde (0.195 g., 78% yield). Infra-red and proton NMR spectroscopy were in agreement with the proposed structure.

What we claim is:

1. 2,3-disubstituted levulinaldehydes of the general formula

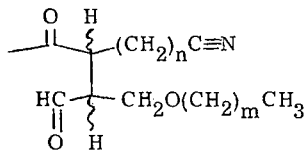

wherein $n$ represents an integer from 5 to 8 inclusive and $m$ represents zero or an integer from 1 to 5 inclusive.

2. A 2,3-disubstituted levulinaldehyde according to claim 1 wherein $n$ is 6 and $m$ is zero.

* * * * *